(12) United States Patent
Ashman

(10) Patent No.: US 7,722,650 B2
(45) Date of Patent: May 25, 2010

(54) VARIABLE ANGLE SPINAL IMPLANT CONNECTION ASSEMBLY

(76) Inventor: Richard B. Ashman, 1407 First St., New Orleans, LA (US) 70130

( * ) Notice: Subject to any disclaimer, the term of this patent is extended or adjusted under 35 U.S.C. 154(b) by 1180 days.

(21) Appl. No.: 10/987,196

(22) Filed: Nov. 12, 2004

(65) Prior Publication Data

US 2005/0113835 A1 May 26, 2005

Related U.S. Application Data

(60) Provisional application No. 60/520,510, filed on Nov. 14, 2003.

(51) Int. Cl.
*A61B 17/70* (2006.01)
(52) U.S. Cl. ...................................... 606/265
(58) Field of Classification Search .................. 606/246, 606/250–253, 264–267, 270, 272, 273, 274, 606/278, 279
See application file for complete search history.

(56) References Cited

U.S. PATENT DOCUMENTS

| 5,047,029 A | 9/1991 | Aebi et al. |
| 5,261,909 A | 11/1993 | Sutterlin et al. |
| 5,282,801 A | 2/1994 | Sherman |
| 5,611,800 A * | 3/1997 | Davis et al. ................. 606/250 |
| 5,688,272 A * | 11/1997 | Montague et al. ........... 606/252 |
| 6,569,164 B1 * | 5/2003 | Assaker et al. .............. 606/250 |

* cited by examiner

*Primary Examiner*—Anu Ramana
(74) *Attorney, Agent, or Firm*—Maginot Moore

(57) ABSTRACT

A variable angle connector for engaging a bone fastener to a spinal rod includes a body defining a channel for receiving the spinal rod and a set screw arrangement for clamping the rod within the channel. The body defines an engagement face configured for interdigitating engagement with the head of the bone fastener. The fastener is mounted on a post projecting from the engagement face of the body, with means for engaging the fastener to the post. The body of the connector includes a deformable portion at one portion of the engagement face that deforms when the set screw is tightened to clamp the rod within the rod channel. As the connector body deforms, the portion of the engagement face is brought into engagement with the head of the bone fastener.

11 Claims, 3 Drawing Sheets

VARIABLE ANGLE SPINAL IMPLANT CONNECTION ASSEMBLY

BACKGROUND OF THE INVENTION

The present invention relates generally to the field of spinal implant systems, and particularly to systems that employ elongated spinal implants, such as rod and plates, connected at various locations along the spinal column. More particularly, the invention concerns a connection assembly that provides variable angle adjustability to the elongated spinal implant relative to a bone fastener engaged to the spine, independent of the adjustment of the bone fastener along the length of the elongated spinal implant.

Several spinal fixation systems have been developed for use in correcting and stabilizing sections of the spinal column and facilitating spinal fusion. In one such system, a bendable elongated spinal implant, such as a rod, is longitudinally disposed adjacent the vertebral column and then secured to various vertebrae along the length of the column by way of a number of bone fasteners of fixation elements. A variety of bone fasteners can be utilized, such as hooks or bone screws, which are configured to engage specific portions of a vertebra.

An example of one such system is the TSRH® Spinal System of Sofamor Danek Group, Inc. In this system, various hooks and bone screws are engaged to a spinal rod by way of eyebolts. In early versions of the TSRH® Spinal System, the vertebral hooks and bone screws were attached to the spinal rod at a fixed orientation, usually projecting perpendicularly below the rod. At the time, the TSRF® Spinal System presented a significant advance over prior systems in its VERSATILITY, strength of fixation, and ease of implantation.

However, one drawback faced by the original TSRH® Spinal System, as well as the other prevalent fixation systems, was that the surgeon was required to make significant adjustments to the contour of the bendable rod so that the bone fasteners could solidly engage the vertebra bodies. What was needed, then, was a bone fastener that could be connected to the spine at a variable angle. In order to address this need, the TSRH® Variable Angle Screw was developed, as described in U.S. Pat. No. 5,261,909. As shown in FIG. 1, this Variable Angle System 10 utilized the same TSRH® eyebolt 12 to achieve a connection between a bone fastener or screw 14 and a spinal rod R. In addition, the Variable Angle System 10 incorporated a washer 16 that fit over the eyebolt 12, engaged the spinal rod R within a groove in one surface of the washer, and provided a radially splined surface 18 facing the bone fastener 14. The bone fastener 14 had a complementary splined surface 20 so that the fastener could be situated at variable angular orientations relative to the spinal rod. A nut 22 threaded onto the post 24 of the eyebolt 12 clamped all the components together to complete the assembly.

The Variable Angle Screw system of the '909 patent presented a significant advance over prior rod-based implant systems. The system of the '909 patent was relatively compact and required a minimal number of parts, yet was able to accomplish a solid fixation of the bone fasteners to the rod at a wide range of angular orientations. One drawback of the system was that the eyebolt-nut combination tightened both the connection along the length of the spinal rod and the angular orientation of the bone fastener together at the same time.

A top-tightening assembly disclosed in U.S. Pat. No. 5,282,801 describes a clamp assembly 30, as depicted in FIG. 2, that replaced the eyebolt and nut with a clamp body 32 having a T-bar 34 against which the head of a variable angle bone fastener was clamped. In addition, while the original TSRH® System relied upon tightening a nut against the variable angle bone screw, the top-tightening approach of the '801 patent utilized a set screw 36 that acted against the spinal rod R disposed within channel 40 to push the spinal rod into the interlocking washer 38, and ultimately against a complementary splined face of the variable angle screw. With this system, the variable angle capability was retained, while a top-tightening feature was added. However, both the '909 and '801 patents describe assemblies that tighten and fix both the connection along the length of the spinal rod and the angular orientation of the bone fastener together at the same time.

With the addition of the top-tightening capability, the more recent TSRH® Spinal System has provided surgeons with a great deal of flexibility in the placement and orientation of bone fasteners, such as hooks and screws, relative to a spinal rod. The variable angle components greatly reduce the need to manipulate and bend the spinal rod to conform to the patient's anatomy. Even with the great improvements presented by the TSRH® Spinal System, certain surgical situations require the connection between the bone fastener and the spinal rod to be carried out in stages—i.e., locking the angular orientation of the bone fastener first, then fixing the connection along the length of the spinal rod, or vice versa.

One approach of achieving independent locking of the location of the bone fastener both along the length of the spinal rod and the locking of the fastener's angular orientation was a spinal implant device known as the Synthes Fixature Intern. This assembly, as described in U.S. Pat. No. 5,047,029, includes a threaded spinal rod over which a connector is placed between two nuts. On the connector there is a face spline clamp assembly for a Schantz-type screw. This device does not adequately serve the needs of spinal surgeons since the rods cannot be bent and still allow the nuts to be manipulated and it is difficult to place more than two bone fasteners on each rod, due to their size. There remains a need for a connector assembly that can accommodate various bone fasteners, while permitting locking the position along the spinal rod and the angular orientation of the bone fastener independently of each other, while addressing the drawbacks of the prior systems.

SUMMARY OF THE INVENTION

To address this need, the present invention contemplates a connector assembly that includes an open channel and set screw for clamping on to a spinal rod independently of a variable angle clamp. The variable angle clamp is configured to engage a mating variable angle bone fastener or a clamping mechanism to affix the shank of a Schantz-type bone fastener. The clamp mechanism for the Schantz-type bone fastener includes a pair of clamp halves forming a slot therebetween that intersects a clamping bore configured to receive the bone fastener. Thus, the clamp can be in the form of a split clamp in which the clamp halves are compressed together to reduce the bore and provide a clamping force on the shank of the bone fastener within the bore.

In one feature of the preferred embodiment of the invention, the connector defines a channel that is configured to receive the spinal rod. Intersecting this channel, and off-center from the axis of the spinal rod, is a set screw which provides a means for securing the connector to the rod. Further, the connector can include a threaded post and a face with radiating splines which can be mated with a variable angle fastener of the type described in U.S. Pat. No. 5,261,909, the disclosure of which is incorporated herein by reference. However, the connector can alternatively be configured to mate with other connectors or clamps that provide a means to connect the clamp, and ultimately the bone fastener, to an elongated implant, such as a spinal rod.

The connector includes an outer surface against which a clamping force is applied to compress a variable angle feature against the bone-engaging fastener or bone-engaging clamp assembly. In a preferred embodiment, this feature can include radiating splines that are configured to interdigitate with similar radiating splines on a component of the variable angle connector. The outer surface of a variable angle screw as described in the '909 patent or the other clamp half can provide a pressure surface and need not, but may, include similar variable angle features.

In accordance with certain features of the invention, the variable angle clamp can be mounted on the shank of a bone-engaging fastener with the open channel exposed. A connector mounted on an elongated implant, such as a spinal rod, can be manipulated to engage the channel of the clamp. The clamp is juxtaposed with the connector at whatever orientation is assumed by the bone-engaging fastener. The entire assembly is tightened by engaging the connection to the elongated implant first, then compressing the clamp halves or variable angle screw via a nut mounted on the threaded shank. Conversely, the clamp which compresses the variable angle screw or clamp may be engaged first, followed by the connection to the elongated implant.

In one important aspect of the present invention, the connector is configured to include a bendable portion carrying the interdigitating or splined features. When the set screw is tightened against the rod within the rod-receiving channel, the bendable portion of the connector deflects so that the interdigitating features come into contact with the like interdigitating features on the head of the bone fastener. Thus, in accordance with this feature of the invention, the final clamping force between the variable angle fastener and the connector is achieved by final tightening of the set screw.

One object of the invention is to provide a variable angle clamp for use with a bone-engaging fastener having a shank, such as a Schantz-type fastener or a variable angle screw fastener with a channel and radiating splines. Another object is achieved by features that allow individual and independent tightening of the connection along the rod and the connection to the bone fastener.

One benefit of the present invention is that it can be readily used to engage a bone fastener to a spinal rod, for instance. A further benefit is that the inventive variable angle clamp can assume various orientations to facilitate overall assembly of the clamp, connector, spinal rod and bone-engaging fastener.

Other objects and benefits of the invention will become apparent from the following written description taken together with the accompanying figures.

DESCRIPTION OF THE PREFERRED EMBODIMENTS

Figure 1:
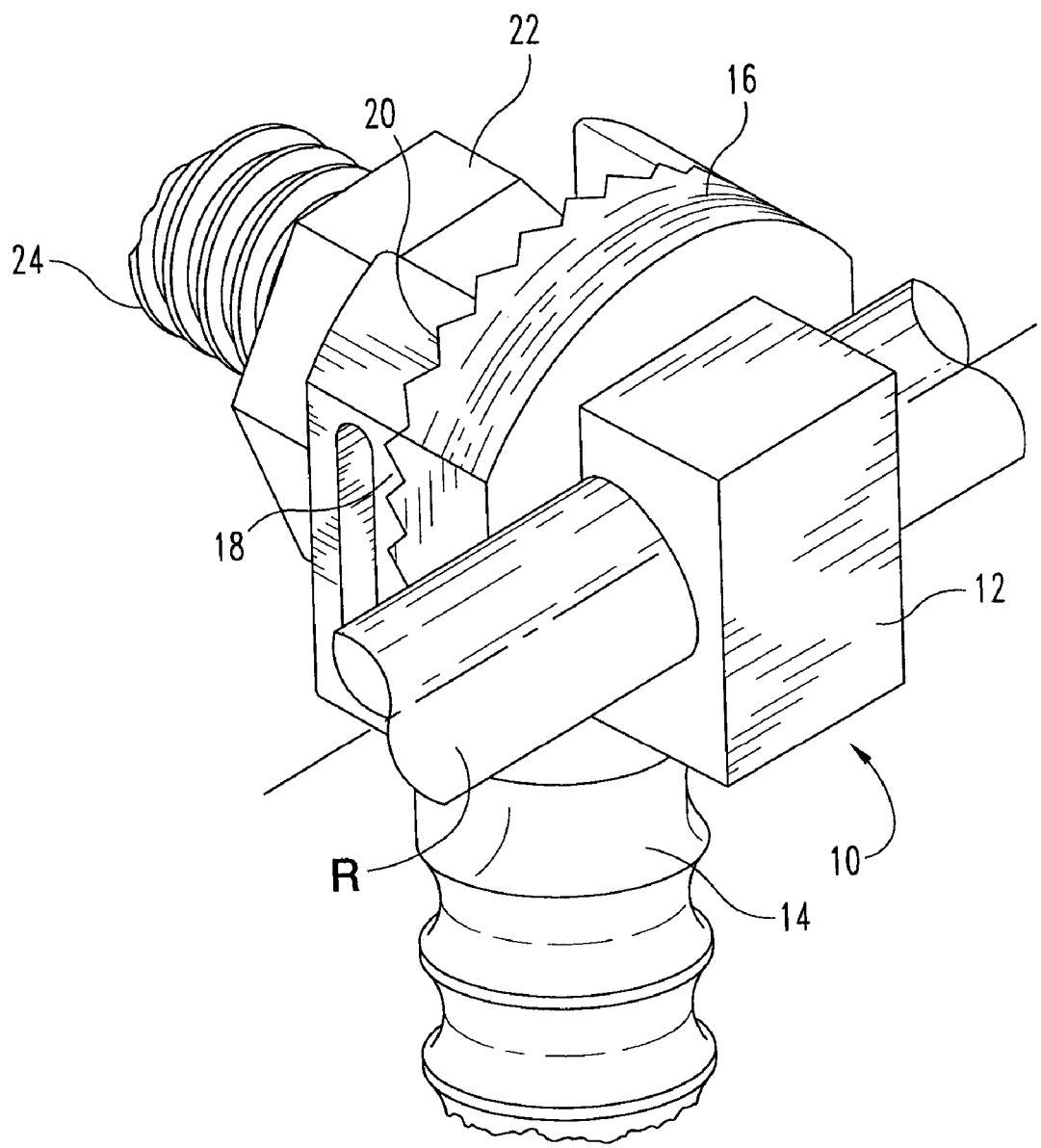
FIG. 1 is a perspective view of a variable angle system as shown in U.S. Pat. No. 5,261,909.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
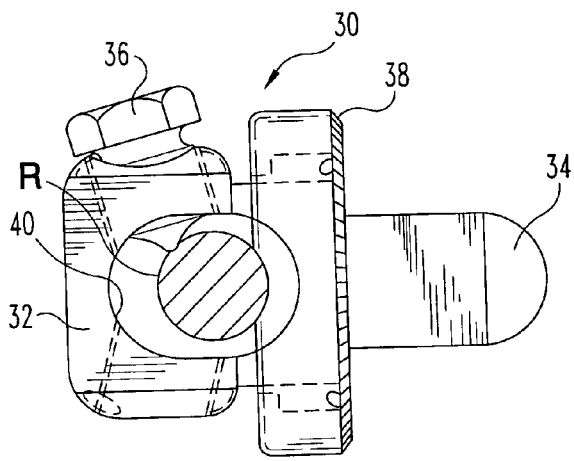
FIG. 2 is a side view of a variable angle system as shown in U.S. Pat. No. 5,282,801.
Figure 3:
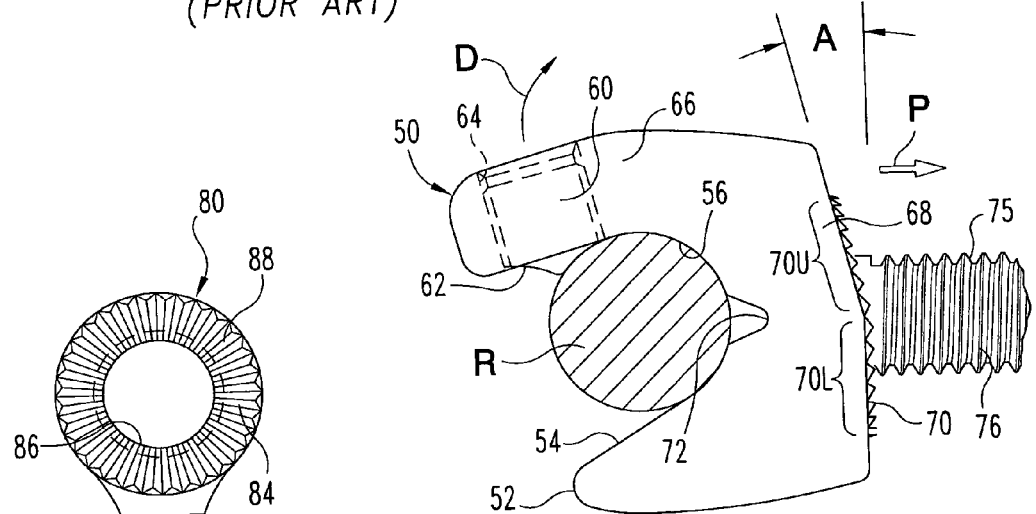
FIG. 3 is a side view of a variable angle connector in accordance with one embodiment of the present invention.

In accordance with one embodiment of the invention, a connector 50 is provided, as shown in FIG. 3, for engagement to an elongated spinal element, such as a spinal rod R. The connector 50 includes a body 52 that defines a channel 54 for reception of the spinal rod R therein. In the preferred embodiment, the channel is open and defines an interior recess 56 against which the rod R is seated when the connector is finally fixed to the rod. Alternatively, the channel 54 can be a closed channel, similar to the channel 40 in the prior art connector shown in FIG. 2. The embodiment shown in FIG. 3 allows the connector 50 to be mounted on a spinal rod in situ. On the other hand, the closed channel requires that the connector be pre-positioned on the rod before introduction.

As shown in FIG. 3, a set screw 60 intersects the channel 54 and includes a tip 62 configured to bear against the rod R. The set screw 60 is threaded through a bore 64 that is arranged relative to the channel 54 to push the rod into the recess 56 with sufficient force to prevent relative movement between the connector 50 and the rod R.

Figure 4:
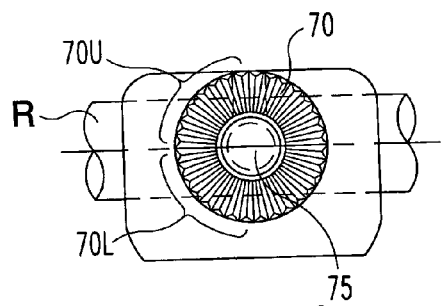
FIG. 4 is a front view of the variable angle connector shown in FIG. 3.

As shown in FIGS. 3 and 4, the set screw bore 64 is defined in an upper body portion 66. This upper body portion 66 is connected to or integral with a bendable portion 68. This bendable portion 68, together with a lower portion of the body 52, define an engagement face 70 that is configured for interdigitating engagement with a complementary face on a bone fastener (such as the fasteners shown in FIGS. 5 and 6). As shown best in FIG. 4, the engagement surface 70 can include a plurality of radiating splines, akin to the splines described in the '909 patent incorporated by reference above.

Further, as shown in FIGS. 3 and 4, the engagement face 70 can be separated into upper and lower faces $70_U$ and $70_L$, respectively. The upper face $70_U$ is angled away from the plane of the lower face $70_L$ at an angle a toward the upper body portion 66. The present invention contemplates that the upper body portion 66, and more particularly the bendable portion 68, is configured so that the upper face $70_U$ can rotate or pivot into alignment with the lower face $70_L$. In accordance with one aspect of the present invention, when the set screw 60 is threaded into the bore 64 and driven into contact with the rod R, the upper body portion 66 deflects upward in the direction of the arrow D in reaction to the pressure being applied to the rod. This upward deflection of the upper body portion causes the bendable portion 68 to pivot in the direction of the arrow P in FIG. 3 until the upper face $70_U$ is generally planar with the lower face $70_L$. Thus, when the set screw 60 is finally tightened, the resulting reaction causes the upper face $70_U$ to bend into engagement with a fastener engaged to the connector as described herein.

In one embodiment, only the upper face $70_U$ of the engagement face 70 is provided with interdigitating features, such as radiating splines. The lower face $70_L$ can present a smooth surface so that it does not impede relative movement between the fastener and the connector until the assembly has been finally tightened.

Figure 5:
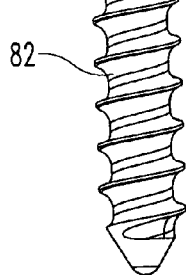
FIG. 5 is a front view of a bone fastener configured for use with the variable angle connector shown in FIGS. 3 and 4.
Figure 6:
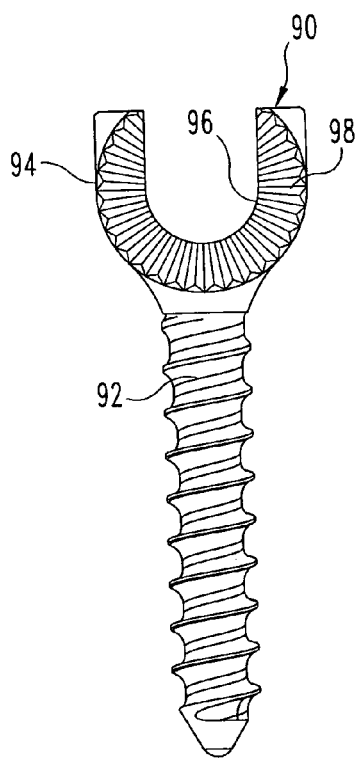
FIG. 6 is a front view of an alternative bone fastener configured for use with the variable angle connector shown in FIGS. 3 and 4.

The connector 50 includes a post 75 that projects from the engagement face 70, as shown in FIG. 3. Preferably, the post is concentrically disposed within the engagement face 70, especially when the face includes radiating splines. In the preferred embodiment, the post 75 includes threads 76. The threaded post 75 provides means for engagement of a bone fastener, such as the fastener 80 shown in FIG. 5. The bone fastener 80 includes a bone engaging portion 82, which can be configured as a bone screw, as shown in FIG. 5, or as a spinal hook for engaging the exterior of a bony feature of the vertebra.

In the illustrated embodiment, the fastener 80 includes a head 84 that defines a central bore 86. In one embodiment, the bore 86 includes internal threads that are configured to engage the threads 76 of the post 75. Thus, with this embodiment of the bone fastener 80, the fastener can be threaded onto the post 75 until the engagement face 88 of the head 84 of the fastener is juxtaposed with the engagement face 70 of the connector body 52. The engagement face 88 of the fastener can include an interdigitating feature that is complementary to the interdigitating feature on the engagement face 70—i.e., radiating splines in the illustrated embodiment. Preferably, the interdigitating feature on the fastener head extends substantially entirely around the engagement face 88 of the fastener to allow the fastener to assume virtually any angular orientation relative to the connector 50.

Where the fastener 80 includes an internally threaded opening 86, it may be preferably for the lower face $70_L$ to be barren of any interdigitating feature, as described above. With this configuration, the head 84 of the fastener can be threaded completely onto the post 75 until the engagement face 88 contacts the lower face $70_L$. The relative vertical angle of the fastener can be adjusted by threading or unthreading the fastener on the post 75. The final fixation occurs when the bendable portion 68 pivots, forcing the upper face $70_U$ into interdigitating contact with the engagement face 88 of the fastener.

It is understood that the fastener 80 must be pre-loaded onto the post 75 of the connector 50. In an alternative embodiment, the fastener can be configured for top loading, like the fastener 90 shown in FIG. 6. With this configuration, the bone engagement portion 92 can be already engaged to the spine before the connector 50 is introduced. Moreover, if the connector includes an open channel 54, as shown in FIG. 3, the spinal rod R can be pre-positioned adjacent the spine and the connector manipulated to couple the rod R and the fastener 90.

Figure 7:
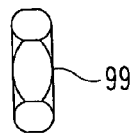
FIG. 7 is a side view of a nut for engaging the bone fastener of FIG. 6 to the variable angle connector of FIGS. 3 and 4.

The fastener 90 includes a head 94 that defines an open channel 96 for receiving the post 75 therein. The head includes an engagement face 98 that can be configured like the engagement faces described above for interdigitating engagement with the engagement face 70 of the connector 50. Since the fastener 90 does not include any element for fixation to the post 75, a nut 99, as shown in FIG. 7, is provided for threaded engagement with the post 75. Thus, the head 94 of the fastener 90 can be trapped between the connector body 52 and the nut 99 as the nut is tightened onto the post 75. It is contemplated that the closed head 84 of the fastener 80 can also be clamped by a nut 99 when the opening 86 is not threaded.

With the fastener 90 and nut 99, the fastener can be tightened onto the post 75 prior to tightening the set screw 60 against the spinal rod. Thus, the vertical angular orientation of the fastener 90 can be adjusted independent of the fixation of the connector 50 to the rod R The angular orientation is fixed when the set screw is tightened, causing the upper face $70_U$ to pivot in the direction P so that the interdigitating features on the connector and fastener can engage each other.

In the embodiment illustrated in FIG. 3, the bendable portion 68 can be a region of reduced thickness relative to the remainder of the body 52. In one specific embodiment, the rod recess 56 can extend into the bendable portion 68 to reduce the thickness of the body at that portion. In another embodiment, the connector body 52 can define a cut-out region 72 at the base of the rod recess 56. This cut-out region can act as a hinge as the bendable portion 68 pivots in the direction P when the set screw 60 is tightened. In both specific embodiments, it is contemplated that the rod recess 56 can be slightly pinched—i.e., slightly smaller in diameter than the rod—so that the rod will assist in deflecting the upper body portion 66 in the direction D as the tip 62 of the set screw 60 pushes the rod R deeper into the recess 56.

Figure 8:
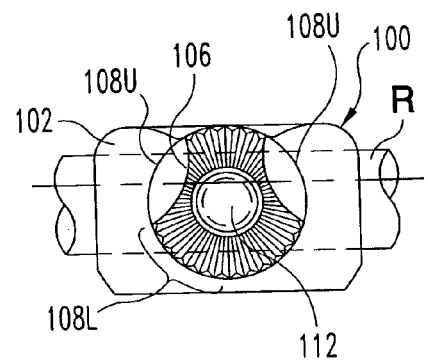
FIG. 8 is a front view of a variable angle connector in accordance with a further embodiment of the invention.
Figure 9:
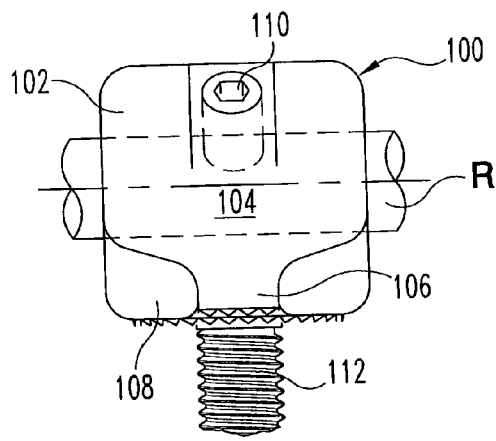
FIG. 9 is a top view of the variable angle connector shown in FIG. 8.

A connector 100, shown in FIGS. 8-9, can include a body 102 that defines a reduced stiffness portion 106. This reduced stiffness portion is essentially necked down from the upper body portion 104 toward the engagement face 108. In this embodiment, the upper portion $108_U$ of the engagement face presents a reduced width relative to the lower portion $108_L$. The connector 100 includes a set screw 110 and post 112 that are similar to the like components in the embodiment of FIG. 3. The connector 100 functions in substantially the same way as the connector 50 described above. The principal difference between the two embodiments is in the manner in which the bendable portion is created.

Figure 10:
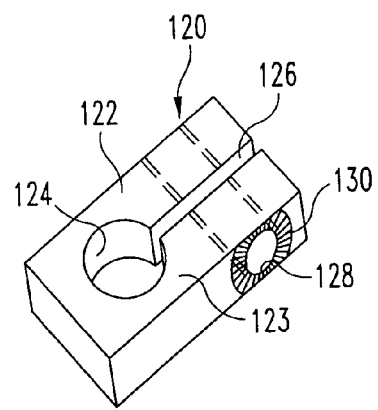
FIG. 10 is a perspective view of a clamp configured for engaging a Schantz-type fastener to the variable angle connectors shown in FIGS. 3-4 or FIGS. 8-9.

While the connectors 50 and 100 are shown for use with the fasteners 80 and 90, the connectors can engage a separate clamp, such as the clamp 120 shown in FIG. 10. The clamp 120 is configured to engage a Schantz-type fastener, meaning a fastener having an elongated proximal shank. The clamp 120 includes two clamp halves 122, 123 that together define a bore 124 for receiving the proximal shank of the Schantz-type fastener. The halves 122, 123 are separated by a gap 126 that is closed when the clamp halves 122, 123 are tightened together. As is known for clamps of this type, closing the gap 126 clamps the proximal shank within the bore 124 as the effective diameter of the bore is reduced.

The clamp 120 includes a bore 128 passing through the clamp halves 122, 123 and across the gap 126. This bore 128 is sized to fit over the posts 75 (FIG. 3) or 112 (FIG. 9). One of the clamp halves 123 defines an engagement face 130 surrounding the bore 128 which is configured to interdigitate with the engagement faces 70 or 108. The nut 99 (FIG. 7) can be used to engage the clamp 120 to the posts 75, 112 and tighten the clamp halves 122, 123 about the proximal shank of the Schantz-type fastener. The face 130 permits positioning of the clamp at variable angular positions so that the Schantz-type fastener can assume variable vertical orientations relative to the spinal rod R.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:

1. A variable angle connector for connecting a fastener, having a head and a bone engagement portion, to a spinal rod at variable angular orientations, comprising:
    a body defining a channel for receiving the spinal rod therein and a threaded bore intersecting the channel;
    a set screw threadedly engagable within said threaded bore and configured to contact the spinal rod therein to clamp the rod within said channel;
    a surface of said body defining an engagement face having a post projecting therefrom, the post configured to be engaged by the head of the fastener;
    means for engaging the head of the fastener to said engagement face; and
    a bendable portion in said body, said bendable portion carrying a portion of said engagement face, wherein said bendable portion is configured to bend when said set screw clamps the rod within said channel so that said portion of said engagement face is brought into engagement with the head of the fastener.

2. The variable angle connector of claim 1, wherein said engagement face of said body includes two portions arranged in planes that are angled relative to each other.

3. The variable angle connector of claim 1, wherein:
    said body includes an interior recess defined by said channel, said recess configured for contacting the rod, said body having a thickness between said interior recess and said engagement face; and
    said bendable portion is formed by a portion of said body at said interior recess that has a reduced thickness compared to said thickness of said body between said interior recess and said engagement face.

4. The variable angle connector of claim 3, wherein:
    said engagement face of said body includes two portions arranged in planes that are angled relative to each other; and
    one of said portions of said engagement face is arranged on said bendable portion.

5. A variable angle connector for connecting a fastener, having a head and a bone engagement portion, to a spinal rod at variable angular orientations, comprising:
    a monolithic body defining a channel for receiving the spinal rod therein and a threaded bore intersecting the channel;
    a set screw threadedly engagable within said threaded bore and configured to contact the spinal rod therein to clamp the rod within said channel;
    a surface of said monolithic body defining an engagement face, said monolithic body further including a post integral with and projecting away from said surface such that the post is external to the monolithic body, the post configured to be engaged by the head of the fastener;
    means for engaging the head of the fastener to said post; and
    means for engaging said engagement face with the head of the fastener by tightening said set screw within said threaded bore.

6. An implant for engagement to a spinal rod comprising:
    a monolithic body defining a channel for receiving the spinal rod therein;
    said monolithic body defining an engagement face, and including a threaded post integral with and projecting away from said engagement face such that the threaded post is external to the monolithic body; and
    a bone fastener having a bone engaging portion and a head, said head defining a threaded bore configured to be threaded onto said threaded post until said head engages said engagement face.

7. The implant of claim 6, wherein said bone engaging portion defines a longitudinal axis and said threaded bore includes an axis that is perpendicular to said longitudinal axis.

8. A method for engaging a fastener to a spinal rod comprising the steps of:
    mounting a monolithic body on the spinal rod, the monolithic body having a channel for receiving the rod, an engagement face and a post integral with and projecting away from the engagement face such that the post is external to the monolithic body;
    engaging the head of a fastener on the post with the head in contact with the engagement face; and
    fixing the spinal rod within the channel so that the monolithic body deforms at the engagement face to engage the engagement face with the head of the fastener.

9. A method for engaging a fastener to a spinal rod comprising the steps of:
    mounting a monolithic body on the spinal rod, the monolithic body having a channel for receiving the rod, an engagement face and a post integral with and projecting away from the engagement face such that the post is external to the monolithic body;
    initially engaging the head of a fastener on the post with the head in contact with the engagement face; and
    finally fixing the engagement face of the monolithic body with the head of the fastener by deformation of the monolithic body at the engagement face.

10. A variable angle connector for connecting a fastener, having a head and a bone engagement portion, to a spinal rod at variable angular orientations, comprising:
    a body defining a channel for receiving the spinal rod therein and a threaded bore intersecting the channel;
    a set screw threadedly engagable within said threaded bore and configured to contact the spinal rod therein to clamp the rod within said channel;
    said body defining an engagement face having a post projecting therefrom, the post configured to be engaged by the head of the fastener;
    means for engaging the head of the fastener to said engagement face; and
    a bendable portion in said body, said bendable portion carrying a portion of said engagement face, whereby said bendable portion is configured so that said portion of said engagement face is brought into engagement with the head of the fastener when said set screw is tightened within said threaded bore, wherein said bendable portion includes a cut-out defined in said channel.

11. The variable angle connector of claim 10, wherein said post defines a longitudinal axis and said cut-out is aligned with said longitudinal axis.

* * * * *